United States Patent
Dernbach et al.

(10) Patent No.: US 7,060,861 B2
(45) Date of Patent: Jun. 13, 2006

(54) METHOD FOR HYDRATING POLY-OR MONOMETHYLOL ALKANALS

(75) Inventors: Matthias Dernbach, Dossenheim (DE); Michael Koch, Speyer (DE); Gerhard Schulz, Bad Düekheim (DE); Hagen Weigl, Ladenburg (DE); Steffen Maas, Bubenheim (DE)

(73) Assignee: BASF Aktiengesellschaft, Ludwigschafen (DE)

( * ) Notice: Subject to any disclaimer, the term of this patent is extended or adjusted under 35 U.S.C. 154(b) by 236 days.

(21) Appl. No.: 10/399,502

(22) PCT Filed: Nov. 2, 2001

(86) PCT No.: PCT/EP01/12681

§ 371 (c)(1),
(2), (4) Date: Apr. 17, 2003

(87) PCT Pub. No.: WO02/38525

PCT Pub. Date: May 16, 2002

(65) Prior Publication Data

US 2004/0044256 A1   Mar. 4, 2004

(30) Foreign Application Priority Data

Nov. 8, 2000   (DE) ................ 100 55 180

(51) Int. Cl.
   *C07C 33/26* (2006.01)
   *C07C 27/00* (2006.01)
   *C07C 31/18* (2006.01)
(52) U.S. Cl. ............. 568/811; 568/814; 568/852; 568/863
(58) Field of Classification Search ........ 568/811, 568/814, 852, 863
See application file for complete search history.

(56) References Cited

U.S. PATENT DOCUMENTS

| | | | | |
|---|---|---|---|---|
| 6,187,971 B1 | 2/2001 | Kratz | ............ | 568/853 |
| 6,201,160 B1 | 3/2001 | Brudrmueller | ......... | 568/862 |
| 6,207,865 B1 | 3/2001 | Breitscheidel | ........... | 568/705 |

FOREIGN PATENT DOCUMENTS

| | | |
|---|---|---|
| WO | 95/32171 | 11/1995 |
| WO | 98/28253 | 7/1998 |
| WO | 99/03801 | 1/1999 |
| WO | 99/44974 | 9/1999 |

OTHER PUBLICATIONS

Tong et al. Adsorption of Metal Ions on a New Chelating Ion-Excahnge Resin Chemically Derived from Chitosan. Chemistry Letters, 1991, (9), p 1529-1532.*

* cited by examiner

*Primary Examiner*—Sikarl A. Witherspoon
(74) *Attorney, Agent, or Firm*—Jason D. Voight

(57) ABSTRACT

In a process for the catalytic hydrogenation of a polymethylolalkanal or a monomethylolalkanal of the formula (I)

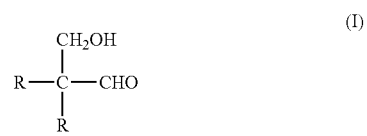

where R may be identical or different and are each a substituted or unsubstituted aliphatic hydrocarbon having from 1 to 22 carbon atoms, an aryl or arylalkyl group having from 6 to 22 carbon atoms or a methylol group, in the presence of a copper-containing catalyst, the hydrogenation feed comprising the polymethylolalkanal or monomethylolalkanal has a total content of metal ions of groups 3 to 14 of the Periodic Table of the Element of up to 5 ppm.

11 Claims, No Drawings

METHOD FOR HYDRATING POLY-OR MONOMETHYLOL ALKANALS

This application is the national stage application of PCT/EP01/12681, filed Nov. 02, 2001, and published on May 16, 2002 as WO 02/038525.

The present invention relates to the field of industrial organic chemistry. More precisely, the present invention relates to a process for the catalytic hydrogenation of polymethylolalkanals or monomethylolalkanals in the presence of a copper catalyst.

The condensation of formaldehyde with CH-acid higher alkanals to form methylolalkanals, generally dimethylolalkanals and trimethylolalkanals, and conversion of the compounds obtained into polyols is a widely practiced process in chemistry. Examples of important triols obtained in this way are trimethylolpropane, trimethylolethane and trimethylolbutane, which have found wide application in the production of surface coatings, urethanes and polyesters. Further important compounds are pentaerythritol, obtainable by condensation of formaldehyde and acetaldehyde, and also neopentyl glycol from isobutyraldehyde and formaldehyde. The tetrahydric alcohol pentaerythritol is likewise frequently used in the surface coatings industry, but has also achieved great importance in the production of explosives.

The polyols mentioned can be prepared by various methods. One method is the Cannizzaro process which is further subdivided into the inorganic Cannizzaro process and the organic Cannizzaro process. Both variants have the disadvantage that, apart from the formation of by-products which are difficult to separate off, one equivalent of formaldehyde is lost.

The disadvantages of the Cannizzaro process are avoided by the hydrogenation process which is known from WO 98/28253. Here, formaldehyde is reacted with the appropriate alkanal in the presence of catalytic amounts of an amine. This stops the reaction at the methylolalkanal stage. After the formaldehyde has been separated off, the reaction mixture, which comprises not only the respective alkanal but also small amounts of the corresponding triol, is subjected to hydrogenation to give the desired polyol.

The catalytic hydrogenation of methylolalkanals in suspension or fixed-bed processes has been known for a long time. Industrial plants virtually all employ fixed-bed catalysts.

As fixed-bed catalysts, it is possible to use not only catalysts of the Raney type as are described, for example, in WO 99/03801 but also, in particular, supported catalysts, for example copper, nickel or noble metal catalysts.

WO 99/44974 describes the hydrogenation of carbonyl compounds, including polymethylolalkanals or monomethylolalkanals, to alcohols over $TiO_2$-supported Cu catalysts.

WO 95/32171 discloses copper catalysts on $SiO_2$-containing supports suitable for the hydrogenation of polymethylolalkanals or monomethylolalkanals.

It is an object of the present invention to provide a process for the catalytic hydrogenation of polymethylolalkanals or monomethylolalkanals which makes it possible to achieve not only high conversions and selectivities but also a long catalyst operating life.

We have found that the content of metal ions of groups 3 to 14 of the Periodic Table of the Elements in the polymethylolalkanals or monomethylolalkanals or the hydrogenation feed comprising polymethylolalkanals or monomethylolalkanals has a significant influence on the achieved conversion and the selectivity of the hydrogenation over copper-containing hydrogenation catalysts and on the operating life of the copper-containing hydrogenation catalysts. For the purposes of the present invention, the hydrogenation feed is the starting material stream which is fed into the hydrogenation and consists of or comprises polymethylolalkanals or monomethylolalkanals.

Accordingly, the abovementioned object is achieved by a process for the catalytic hydrogenation of a polymethylolalkanal or monomethylolalkanal of the formula (I)

where R may be identical or different and are each a substituted or unsubstituted aliphatic hydrocarbon having from 1 to 22 carbon atoms, an aryl or arylalkyl group having from 6 to 22 carbon atoms or a methylol group, in the presence of a copper-containing catalyst, wherein the hydrogenation feed comprising the polymethylolalkanal or monomethylolalkanal has a total content of metal ions of groups 3 to 14 of the Periodic Table of the Elements of up to 5 ppm.

The hydrogenation feed comprising the polymethylolalkanal or monomethylolalkanal of the formula (I) preferably comprises, as elements of groups 3 to 14 of the Periodic Table of the Elements, iron(II), iron(III), chromium(III), chromium(IV) and nickel(II). The total content of metal ions of groups 3 to 14 in the hydrogenation feed comprising polymethylolalkanal or monomethylolalkanals of the formula (I) should not exceed 5 ppm, with the content of each metal ion being, depending on the number of metal ions present, from 0.001 to 5 ppm, preferably from 0.001 to 2 ppm.

The process of the present invention can be employed for hydrogenation of the pure substances or of the monomethylolalkanals and polymethylolalkanals in admixture with other compounds. Since the respective polymethylolalkanals or monomethylolalkanals are prepared, for example, by Aldol reaction of the appropriate aliphatic aldehydes with formaldehyde in the presence of a basic catalyst as described in WO 98/28253, the output from this reaction could be passed directly to the hydrogenation to form the corresponding polyols.

Prior purification of this reaction product is known, for example, from the German patent application No. 199 63 445.9, in which the removal of formaldehyde is described. Reference may be made, in particular, to Examples 2–4 insofar as they relate to the distillation of the aldolization product, i.e. the polymethylolalkanal of the formula (II). The reaction conditions mentioned in the examples apply analogously to monomethylolalkanals. Removal of metal ions from the reaction product is not described. In addition, polymethylolalkanal or monomethylolalkanal is lost as a result of the distillation.

In general, metal ions get into the polymethylolalkanal or monomethylolalkanal or into the hydrogenation feed comprising polymethylolalkanal or monomethylolalkanol as a result of corrosion of plant components in the aldolization. Polymethylolalkanal or monomethylolalkanal or the hydrogenation feed comprising polymethylolalkanal or monomethylolalkanal having a reduced metal ion content can therefore be obtained, firstly by avoidance of introduction of extraneous metal ions, for example by the choice of suitable metal-free materials such as glass, enamel or high-quality materials such as titanium or high-quality alloys for storage vessels and intermediate vessels, pipes, reactors, distillation columns and rectification columns. Since this can, if it is technically achievable, in particular for industrial plants, be associated with considerable costs, preference is given to reducing the metal ion content by removal of the metal ions from the polymethylolalkanals or monomethylolalkanals and/or the starting materials or process streams required for their preparation, for example the aliphatic aldehydes and formaldehyde used in the aldol reaction for preparing the polymethylolalkanols or monomethylolalkanals.

The removal of the metal ions from the polymethylolalkanals or monomethylolalkanals and/or the starting materials such as formaldehyde or aliphatic aldehydes required for their preparation can be carried out by treatment with adsorbents and/or by complexation and subsequent membrane separation processes, preferably by treatment with adsorbents.

For complexation with subsequent membrane separation processes according to the present invention, the hydrogenation feed is admixed with a highly polymeric, soluble complexing agent which complexes the metal ions present in the feed. As complexing agents, it is possible to use polymers of any type which contain functional groups (for example COOH, $NR_2$, etc.) or heteroatoms such as N or P suitable for complexation. Thus, for example, polyimines of appropriate molar mass can be used. The complexed polymer and the excess of uncomplexed polymer are subsequently separated off from the hydrogenation feed by means of a suitable membrane (organic or inorganic). The membrane retains the complexing agent together with bound metal ions, while the (dissolved) hydrogenation feed passes through the membrane and is subsequently hydrogenated.

As adsorbents, preference is given to using activated carbon, acid or base ion exchangers or mixtures thereof, metal oxides or molecular sieves, with chelating ion exchangers being particularly preferred.

According to the present invention, it has been found that no decomposition of the sensitive polymethylolalkanals occurs on treatment with the adsorbents. This is surprising, since it is known that polymethylolalkanals tend to undergo the retro-aldol reaction, i.e. the reversal of their formation, at elevated temperatures and when treated with bases or acids.

Suitable activated carbons have, for example, a surface area of from 500 to 2000 $m^2/g$ in accordance with DIN 66 131 and a porosity of from 0.05 to 1.0 $cm^3/g$ in accordance with DIN 66134 and are sold by Merck, Darmstadt, by Chemviron Midwest Corp., Wooster, USA, under the trade name CPG LF 8 30 and by Lurgi AG, Frankfurt, under the trade name Carboraffin P®.

Suitable ion exchangers are preferably chelating ion exchangers such as Amberlite® TRL from Rohm & Haas, Darmstadt, Levatit® TP 207 from Bayer AG, Leverkusen, in all possible forms, for example in bead form or as gel.

Metal oxides which can be used are, for example, alpha- or gamma-aluminum oxide, silicon oxide, titanium dioxide in the anatase or rutile modification, zirconium dioxide, magnesium oxide, calcium oxide, zinc oxide or mixtures of metal oxides such as aluminosilicates. Suitable aluminum oxide is marketed by, for example, Condea Chemie AG, Hamburg, under the trade name Pural® SB.

Examples of suitable molecular sieves are aluminosilicates or zeolites having a pore diameter of greater than 3 Å, for example Zeokat® Z 6 01-01-y zeolite or Zeochem® molecular sieve 13×13 zeolite from Uetikon AG, Uetikon, Switzerland.

The adsorbents can be in the form of shaped bodies such as spheres, extrudates, pellets, granules or powder.

In general, the polymethylolalkanal or monomethylolalkanal and/or the starting material required for its preparation whose metal ion content is to be reduced is treated at a temperature between the solidification point and the boiling point of the polymethylolalkanal or monomethylolalkanal or of the starting material required for its preparation, preferably at from 20 to 150° C., particularly preferably from 40 to 100° C., and pressures of from 0.001 to 200 bar, preferably from 0.5 to 10 bar, in a stirred vessel, but preferably by passage through an adsorbent in a fixed bed.

In a particularly preferred embodiment, the polymethylolalkanals or monomethylolalkanals are prepared by means of the aldol reaction from the appropriate aliphatic aldehydes and formaldehyde in the presence of a basic catalyst as described in WO 98/28253, which is hereby expressly incorporated by reference. The reaction product from the aldolization as described in WO 98/28253 is, preferably on the side still under atmospheric pressure, passed directly over a fixed bed of adsorbent, particularly preferably a chelating ion exchanger, and then passed to the hydrogenation to form the corresponding polyols. When using ion exchangers as adsorbent, the manufacturer's recommendations for the optimum temperature range of the respective ion exchanger should be adhered to within the abovementioned temperature ranges.

The residence time of the polymethylolalkanal or monomethylolalkanal or of the starting material required for its preparation is dependent on the affinity of the adsorbent and is generally in the range from 1 minute to 24 hours, preferably from 5 to 30 minutes. The polymethylolalkanal or monomethylolalkanal or the starting material required for its preparation can be used in a solvent, preferably in the form of a 20–60% strength by weight solution. Examples of suitable solvents are water, alcohols such as methanol and ethanol or 0.1–99% strength alcohol/water mixtures. The treatment with adsorbent is preferably carried out in water or in a 0.1–99% strength alcohol/water mixture.

The adsorbent can be regenerated, e.g. depending on the adsorbent, by flushing with water, alkalis or acids and subsequent washing with water. Acid or strong acid ion exchangers are preferably regenerated by means of aqueous hydrochloric acid, sulfuric acid, formic acid or acetic acid, while base or strong base ion exchangers are preferably regenerated with aqueous sodium hydroxide solution, potassium hydroxide solution or $Ca(OH)_2$.

The avoidance of introduction of extraneous metal ions is particularly preferably combined with treatment of the polymethylolalkanals or monomethylolalkanals or the starting materials required for their preparation with an adsorbent.

In the hydrogenation according to the present invention, use is made of copper-containing catalysts, preferably ones selected from among Raney copper catalysts and supported copper catalysts.

Suitable Raney copper catalysts are, for example, the Raney copper catalysts in the form of nuggets as described in WO 99/03801, which is hereby expressly incorporated by reference. These catalysts have a nugget size of from 2 to 7 mm, a copper content of from 40 to 90% by weight, a surface area by the Langmuir method of from 5 to 50 $m^2/g$, a copper surface area of from 0.5 to 7 $m^2/g$, an Hg pore volume of from 0.01 to 0.12 ml/g and a mean pore diameter of from 50 to 300 nm.

Supported copper catalysts suitable for use in the process of the present invention are, for example, the $SiO_2$-supported copper catalysts known from WO 95/32 171, which is hereby expressly incorporated by reference. These catalysts comprise from 5 to 50% by weight of copper, calculated as CuO, preferably from 70 to 95% by weight of silicon, calculated as $SiO_2$, and, if desired, one or more of the elements magnesium, barium, zinc or chromium and are produced by impregnation of a porous silicon dioxide support material with an excess of an aqueous solution of a copper compound which can readily be decomposed thermally, subsequent drying and calcination at from 200 to 400° C.

The hydrogenation of the present invention is particularly preferably carried out in the presence of the catalyst known from WO 99/44974, which is hereby expressly incorporated by reference. This catalyst comprises an inorganic support comprising $TiO_2$ and, as active component, copper or a mixture of copper with at least one metal selected from the group consisting of zinc, aluminum, cerium, noble metals and metals of transition group VIII and has a specific copper surface area of not more than 10 $m^2/g$. The support present in these catalysts is preferably $TiO_2$ or a mixture of $TiO_2$ and $Al_2O_3$ or a mixture of $TiO_2$ and $ZrO_2$ or a mixture of $TiO_2$, $Al_2O_3$ and $ZrO_2$, particularly preferably $TiO_2$. In the production of this catalyst as described in WO 99/44974, metallic Cu powder can be added as further additive during tableting, provided that the copper surface area is not more than 10 $m^2/g$.

The hydrogenation is preferably carried out in a fixed bed. However, continuous or batchwise suspension hydrogenation or a fluidized-bed reaction with upward and downward swirling motion of the catalyst material are likewise possible. The hydrogenation can be carried out in the gas phase or in the liquid phase. The hydrogenation is preferably carried out in the liquid phase, for example in the downflow or upflow mode.

When the downflow mode is employed, the liquid starting material comprising the polymethylolalkanal or monomethylolalkanal to be hydrogenated is allowed to trickle over the catalyst bed located in the reactor, which is under hydrogen pressure, forming a thin liquid film on the catalyst. In contrast, when the upflow mode is employed, hydrogen gas is introduced into the reactor which is flooded with the liquid reaction mixture, so that the hydrogen passes through the catalyst bed in the form of rising gas bubbles.

In one embodiment, the solution to be hydrogenated is pumped over the catalyst bed in a single pass. In another embodiment of the process of the present invention, part of the product is continuously taken off as product stream after passage through the reactor and is optionally passed through a second reactor, as defined above. The other part of the product is fed back into the reactor together with fresh polymethylolalkanal- or monmethylolalkanal-containing starting material. This procedure will hereinafter be referred to as the circulation mode.

If the downflow mode is chosen as embodiment of the process of the present invention, the circulation mode is preferred. The process is more preferably carried out using the circulation mode and a main reactor and an after-reactor, with particular preference being given to operating the main reactor in the circulation mode and the after-reactor in a single pass.

The process of the present invention is suitable for the hydrogenation of polymethylol and monomethylol compounds. Examples are dimethylolethanal, trimethylolethanal (pentaerythrital), 2-methylolpropanal, 2,2-dimethylolpropanal (DMP), 2-methylolbutanal, 2,2-dimethylolbutanal and hydroxypivalaldehyde. Particular preference is given to hydroxypivalaldehyde (HPA), trimethylolethanal (pentaerythrital), 2,2-dimethylolpropanal (DMP) and dimethylolbutanal (DMB).

The polymethylolalkanal or monomethylolalkanal to be hydrogenated can be fed into the hydrogenation reactor either alone or as a mixture with the product of the hydrogenation reaction, either in undiluted form or using an additional solvent. Suitable additional solvents are, in particular, water, alcohols such as methanol, ethanol and the alcohol formed under the reaction conditions. Preferred solvents are water, THF, NMP, and ethers such as dimethyl ether, diethyl ether, MTBE; particular preference is given to water.

The hydrogenation both in the upflow mode and in the downflow mode, in each case preferably using the circulation mode, is generally carried out at from 20 to 250° C., preferably from 70 to 200° C., particularly preferably from 80 to 150° C., and a pressure of from 1 to 350 bar, preferably from 10 to 200 bar, particularly preferably from 20 to 100 bar.

High conversions and selectivities are achieved in the process of the present invention, and the catalysts have a high operating life. The invention is illustrated by the following examples.

EXAMPLES

Preparation of Dimethylolbutyraldehyde

In the following illustrated examples, use was made of an aldolization mixture prepared as follows:

An apparatus comprising two heatable stirred vessels connected to one another by overflow pipes and having a total capacity of 72 l was supplied continuously with fresh, aqueous formaldehyde solution (4300 g/h of a 40% strength aqueous solution), n-butyraldehyde (1800 g/h) and fresh trimethylamine as catalyst (130 g/h) in the form of a 45% strength aqueous solution. The reactors were maintained at 40° C. In this reaction, it is possible to use a low-methanol formaldehyde as is described in the German application DE 199 63 438.6 having the title "Preparation of polyalcohols with methanol-impoverished formaldehyde" (Applicant: BASF AG) of Dec. 28, 1999.

The output was passed directly into a falling film evaporator with superposed column (11 bar steam for heating) and there fractionally distilled under atmospheric pressure to give a low-boiling product consisting essentially of butyraldehyde, ethylacrolein, formaldehyde, water and trimethylamine which was taken off at the top and a high-boiling bottom product.

The product taken off at the top was continuously condensed and recirculated to the above-described reactors.

The high-boiling bottom product from the evaporator (about 33.5 kg/h) was continuously admixed with fresh trimethylamine catalyst (50 g/h in the form of a 45% strength aqueous solution) and fed into a heatable tube reactor provided with packing and having an empty volume of 12 l. The reactor was maintained at 40° C.

The output from the after-reactor was introduced continuously into the upper part of a further disillation apparatus for removal of formaldehyde (11 bar steam for heating) and fractionally distilled there to give a low-boiling product consisting esssentially of ethylacrolein, formaldehyde, water and trimethylamine which was taken off at the top and a high-boiling bottom product. The low-boiling product taken off at the top (27 kg/h) was continuously condensed and recirculated to the first stirred vessel, while the high-boiling bottom product was collected.

The bottom product obtained in this way consisted essentially of water together with dimethylolbutyraldehyde, formaldehyde and traces of monomethylolbutyraldehyde.

The formaldehyde was removed from the bottom product as described in Example 4 of the German Application DE 199 63 445.9 having the title "Removal of formaldehyde from polyol-containing reaction mixtures with the addition of solvents" of Dec. 28, 1999 (Applicant:BASF AG). A 70% strength aqueous product comprising 24% by weight of dimthylolbutyraldehyde (DMB) was obtained.

Determination of the Metal Ion Content 0.5–1 g of a sample of a polymethylolalkanal- or monomethylolalkanal-containing hydrogenation feed was subjected to an acid digestion process in which the sample is admixed firstly with 0.2 ml of an aqueous $Na_2SO_4$ solution (200 g/l of $Na_2SO_4$), then with 8 ml of sulfuric acid (1.84 g/ml) and subsequently with 3 ml of nitric acid (1.41 g/ml) and then heated to boiling. The mixture is then oxidized hot using 10 ml of a mixture of nitric acid, sulfuric acid and perchloric acid in a volume ratio of 2:1:1. After fuming off the excess acids, the residue is made up to 10 ml with dilute hydrochloric acid. The metal ion concentration is determined on this volumetric solution by atomic emission spectroscopy using the inductively coupled plasma method (ICP-AES), for example by means of an IRIS Advantage ICP spectrometer from Thermo-Jarrel Ash.

Examples 1 to 6

A 70% strength aqueous DMB solution (70° C.) prepared by the above method and containing Cr and Ni ions was passed continuously in the upflow mode through a tube reactor charged with various adsorbents. The 30 ml reactor was in each case completely filled with adsorbent, and the DMB solution was fed in at a rate of 30 ml/h. The outputs were collected and analyzed for Cr and Ni. The result is summarized in Table 1.

TABLE 1

| Example | Adsorbent | Cr [ppm] | Ni [ppm] |
|---|---|---|---|
| Starting material | | 13 | 17 |
| 1 | 72281 Pural ® SB (1.5 mm extrudates) | <1 | <1 |
| 2 | $\gamma$-$Al_2O_3$ (3 mm extrudates) | <1 | 1 |
| 3 | Molecular sieve 10Å (spheres) | 1 | <1 |
| 4 | Zeolite (Zeokat ® Z6 01-01 y) | 1 | 8 |
| 5 | $TiO_2$ (3 mm extrudates) | <1 | 11 |
| 6 | Zeolite (Zeochem Molecular sieve 13 × 13) | 3 | <1 |

Examples 7 and 8

These examples were carried out using a method analogous to that for Examples 1 to 6, but a 60 ml reactor was used and the feed rate was 15 ml/h. The result is summarized in Table 2.

TABLE 2

| Example | Adsorbent | Fe [ppm] | Cr [ppm] | Ni [ppm] |
|---|---|---|---|---|
| Starting material | | 50 | 10 | 10 |
| 7 | Chelating ion exchanger (Lewatit ® TP 207) | <1 | <1 | <1 |
| 8 | Chelating ion exchanger (Amberlite ® TRL 218) | <1 | <1 | 1 |

Examples 9 to 11

An aqueous solution of dimethylolpropionaldehyde (dimethylpropionaldehyde content=37.2%) which initially contained 21 ppm of iron ions was stirred with 10% by weight of activated carbon for 15 hours at room temperature. After the activated carbon had been separated off, the Fe concentration was determined in the product. The result is summarized in Table 3.

TABLE 3

| Example No.: | Activated carbon | Concentration of Fe [ppm] |
|---|---|---|
| 9 | Merck (powder) | 1 |
| 10 | Carboraffin P ® | 0.5 |

Comparative Example C1

The dimethylolaldehyde hydrogenation was carried out over 150 ml of catalyst in a fixed-bed reactor (main reactor, circulation mode) and over 50 ml of Cu-$TiO_2$ catalyst in a $2^{nd}$ downstream fixed-bed reactor (after-reactor, single pass). The catalyst was prepared by a method analogous to J in DE 198 09 418. It comprised 42% by weight of CuO, 16% by weight of Cu and 46% by weight of $TiO_2$. The catalyst was activated beforehand at 180° C. using a hydrogen/nitrogen mixture. The hydrogenation of the methylolaldehyde-containing feed stock was carried out in the downflow mode at 120° C., a pressure of 90 bar, a feed rate of 100 ml/h and a circulation in the main reactor of 900 ml/h.

Analysis of the aqueous dimethylolbutyraldehyde (DMB) feed indicated 10 ppm of Ni, 10 ppm of Cr and 3 ppm of Fe. The hydrogenation was operated under these conditions for 12 days. The result is summarized in Table 4.

TABLE 4

| Running time [h] | DMB after main reactor [GC-% by area] | Conversion [%] after main reactor [%] | Selectivity [%] |
|---|---|---|---|
| 24 h | 0.20 | 99.1 | 94.2 |
| 144 h | 0.97 | 95.8 | 93.1 |
| 288 h | 2.66 | 88.4 | 92.6 |

Example 11

A continuous hydrogenation was carried out in a manner analogous to Comparative Example C1 over the same period of time, but a dimethylolbutyraldehyde feed containing 1 ppm of Cr, 1 ppm of Ni and 2 ppm of Fe was used. The result is summarized in Table 5.

TABLE 5

| Running time [h] | DMB after main reactor [GC-% by area] | Conversion [%] | Selectivity [%] |
|---|---|---|---|
| 24 | 0.42 | 98.2 | 94.4 |
| 144 | 0.47 | 98.0 | 94.6 |
| 288 | 0.55 | 97.6 | 94.5 |

Comparison of the result of the example according to the present invention with the comparative example is summarized in Table 6.

TABLE 6

| Example | Metal content of Fe + Cr + Ni | Drop in conversion after 288 h | Drop in selectivity after 288 h |
|---|---|---|---|
| 11 | 4 ppm | 0.6% | 0.1% |
| C1 | 23 ppm | 10.7% | 1.6% |

The comparison shows that the process of the present invention makes it possible to achieve a significantly longer operating life of the catalyst.

We claim:

1. A process for the catalytic hydrogenation of a polymethylolalkanal or a monomethylolalkanal of the formula (I)

(I)

where R may be identical or different and are each a substituted or unsubstituted aliphatic hydrocarbon having from 1 to 22 carbon atoms, an aryl or arylalkyl group having from 6 to 22 carbon atoms or a methylol group, in the presence of a copper-containing catalyst, wherein the hydrogenation feed comprising the polymethylolalkanal or monomethylolalkanal has a total content of metal ions of groups 3 to 14 of the Periodic Table of the Elements of up to 5 ppm.

2. A process as claimed in claim 1, wherein the content of metal ions of groups 3 to 14 of the Periodic Table of the Elements is from 0.001 to 5 ppm.

3. A process as claimed in claim or 2, wherein the metal ion content of the hydrogenation feed comprising the polymethylolalkanal or monomethylolalkanal is set by removal of the metal ions from the polymethylolalkanal or monomethylolalkanal and/or the starting materials required for its preparation by treating with adsorbents and/or by complexation and subsequent membrane separation processes and/or avoidance of the introduction of the metal ions.

4. A process as claimed in any of claims 1 to 3, wherein the adsorbent is selected from among activated carbon, acid and base ion exchangers and mixtures thereof, metal oxides and molecular sieves.

5. A process as claimed in claim 4, wherein the adsorbent is a chelating ion exchanger.

6. A process as claimed in claim 1, wherein the copper-containing catalyst is selected from among Raney copper catalysts and supported copper catalysts on oxidic supports.

7. A process as claimed in claim 1, wherein the copper-containing catalyst comprises an inorganic support comprising $TiO_2$ and, as active component, copper or a mixture of copper with at least one metal selected from the group consisting of zinc, aluminum, ceriuim, noble metals and metals of transition group VIII, and the copper surface area is not more than 10 $m^2/g$.

8. A process as claimed in claim 7, wherein the support material comprises a mixture of $TiO_2$ and $Al_2O_3$ or a mixture of $TiO_2$ and $ZrO_2$ or a mixture of $TiO_2$ and $Al_2O_3$ and $ZrO_2$.

9. A process as claimed in claim 7 or 8, wherein metallic copper powder is added to the catalyst material during shaping to produce pellets.

10. A process as claimed in any of claims 1 to 9, wherein the catalytic hydrogenation is carried out as a fixed-bed reaction in the downflow mode or in the upflow mode.

11. A process as claimed in any of claims 1 to 10 carried out in the circulation mode.

* * * * *